United States Patent [19]

Fleet et al.

[11] Patent Number: 5,041,555
[45] Date of Patent: Aug. 20, 1991

[54] DERIVATIVES OF 1,4-DIDEOXY-1,4-IMINO-D-MANNITOL AND PREPARATION THEREOF

[75] Inventors: George W. J. Fleet, Oxford; Bryan Winchester, London; Neil M. Carpenter, Oxford, all of United Kingdom

[73] Assignee: Monsanto Company, St. Louis, Mo.

[21] Appl. No.: 585,450

[22] Filed: Sep. 21, 1990

Related U.S. Application Data

[63] Continuation of Ser. No. 461,859, Jan. 8, 1990, Pat. No. 4,996,329, which is a continuation-in-part of Ser. No. 424,628, Oct. 20, 1989.

[51] Int. Cl.$^5$ ............................................. C07D 207/12
[52] U.S. Cl. ..................................... 548/541; 548/453
[58] Field of Search ............................... 548/453, 541

[56] References Cited

PUBLICATIONS

Fleet, J. Chem. Soc. Chem. Commun. 1984, pp. 1240–1241.
Bashyal et al., Tetrahedron 43, 3083–3093 (1987).
Fleet et al., FEBS Lett. 237, 128–132 (1988).
Fleet et al., Tetrahedron 44, 2649–2655 (1988).

Primary Examiner—David B. Springer
Attorney, Agent, or Firm—Scott J. Meyer; James W. Williams, Jr.

[57] ABSTRACT

Novel derivatives of 1,4-dideoxy-1,4-imino-D-mannitol and method for their synthesis from 4,5-anhydro-1-azido-1-deoxy-2,3-O-isopropylidene-D-talitol or its triflate derivative are disclosed. The novel derivatives, 6-fluoro-1,4-imino-1,4,6-trideoxy-D-mannitol and the N-butyl and N-benzyl derivatives of 1,4-dideoxy-1,4-imino-D-mannitol, have useful mannosidase inhibitory activity.

4 Claims, No Drawings

DERIVATIVES OF 1,4-DIDEOXY-1,4-IMINO-D-MANNITOL AND PREPARATION THEREOF

CROSS-REFERENCE TO RELATED APPLICATION

This is a continuation of application Ser. No. 07/461,859, filed Jan. 8, 1990, U.S. Pat. No. 4,996,329, which is a continuation-in-part of copending application Ser. No. 07/424,628, filed Oct. 20, 1989.

BACKGROUND OF THE INVENTION

This invention relates to derivatives of 1,4-dideoxy-1,4-imino-D-mannitol and, more particularly, to the novel 6-fluoro-1,4-imino-1,4,6-trideoxy-D-mannitol and a method for its preparation. This novel fluoro derivative of 1,4-dideoxy-1,4-imino-D-mannitol is a powerful inhibitor of mannosidases.

1,4-dideoxy-1,4-imino-D-mannitol is an azofuranose analogue of mannose and is structurally related to swainsonine but lacks the ethano unit connecting the nitrogen to C-6. It is an inhibitor of several mannosidases [Fleet et al., *J. Chem. Soc. Chem. Commun.* 1984, pp. 1240–1241], including glycoprotein mannosidases [Palamarczyk et al., *Arch. Biochem. Biophys.* 35, 243 (1985)].

Synthesis of 1,4-dideoxy-1,4-imino-D-mannitol from benzyl α-D-mannopyranoside is disclosed by Fleet et al., supra., and the full synthesis from D-mannose is described in detail by Bashyal et al., *Tetrahedron* 43, 3083–3093 (1987).

1,4-dideoxy-1,4-imino-D-mannitol and its N-methyl derivative have been tested as antiviral agents against human immunodeficiency viruses (HIV-1 and HIV-2) but with only 10% reduction in the cytopathic effect (CPE) as described by Fleet et al., *FEBS Lett.* 237, 128–132 (1988).

Accordingly, synthesis of derivatives of 1,4-dideoxy-1,4-imino-D-mannitol having strong enzyme inhibitory activity and/or potential anti-viral activity would be desirable.

BRIEF DESCRIPTION OF THE INVENTION

In accordance with the present invention, novel derivatives of 1,4-dideoxy-1,4-imino-D-mannitol and methods of their preparation are provided. The preferred derivatives are the potent mannosidase inhibitor, 6-fluoro-1,4-imino-1,4,6-trideoxy-D-mannitol, and a precursor, 6-fluoro-1,4-imino-2,3-O-isopropylidene-1,4,6-trideoxy-D-mannitol. Other novel derivatives are the N-butyl and N-benzyl derivatives of 1,4-dideoxy-1,4-imino-D-mannitol, which are active but less potent mannosidase inhibitors than the 6-fluoro derivative.

The novel mannosidase inhibitors of this invention have been synthesized in a series of steps from the divergent intermediate, 4,5-anhydro-1-azido-1-deoxy-2,3-O-isopropylidene-D-talitol, or its triflate derivative, 4,5-anhydro-1-azido-1-deoxy-2,3-O-isopropylidene-6-O-trifluoromethanesulfonyl-D-talitol. Synthesis of these two intermediates is disclosed in copending application Ser. No. 07/424,628 filed Oct. 20, 1989. Briefly, the divergent intermediate, 4,5-anhydro-1-azido-1-deoxy-2,3-O-isopropylidene-D-talitol, is derived from mannose by introduction of an azido group at C-1 and by a single inversion at C-4. Thus, diacetone mannose is first converted into the corresponding diol, 1,2:4,5-di-O-isopropylidene-D-mannitol, which in turn is esterified with methanesulfonyl chloride. The resulting dimesylate undergoes relative displacement of the primary mesylate by sodium azide to give an azidomesylate which is then partially hydrolyzed to a diol and the latter material oxidized to the 4,5-anhydro-1-azido-1-deoxy-2,3-O-isopropylidene-D-talitol. The triflate derivative is prepared by esterifying the latter intermediate at the primary hydroxyl with triflic anhydride.

Synthesis of the novel 6-fluoro-1,4-imino-1,4,6-trideoxy-D-mannitol of the present invention from the intermediate triflate is preferably carried out as follows:

(a) 4,5-Anhydro-1-azido-1-deoxy-2,3-O-isopropylidene-6-O-trifluoromethanesulfonyl-D-talitol is reacted with fluoride ion to give the epoxide, 4,5-anhydro-1-azido-1,6-dideoxy-6-fluoro-2,3-O-isopropylidene-D-talitol, (b) The resulting epoxide is catalytically hydrogenated, e.g. with palladium on carbon, to give the fluoride, 6-fluoro-1,4-imino-2,3-O-isopropylidene-1,4,6-trideoxy-D-mannitol, and (c) The isopropylidene protecting group in the resulting fluoride is removed by acid hydrolysis to give the desired 6-fluoro-1,4-imino-1,4,6-trideoxy-D-mannitol.

Synthesis of the novel N-butyl and N-benzyl derivatives of 1,4-dideoxy-1,4-imino-D-mannitol from the divergent intermediate is preferably carried out as follows:

(a) 4,5-Anhydro-1-azido-1-deoxy-2,3-O-isopropylidene-D-talitol is catalytically hydrogenated, e.g. with palladium on carbon, to give the diol, 1,4-dideoxy-1,4-imino-2,3-O-isopropylidene-D-mannitol, (b) The resulting diol is chemically N-alkylated with butanal to form the protected N-butyl derivative or with benzyl bromide to form the protected N-benzyl derivative, (c) The isopropylidene protecting group in the N-butyl or N-benzyl derivative is removed by acid hydrolysis to give, respectively, the desired N-butyl-1,4-dideoxy-1,4-imino-D-mannitol or N-benzyl-1,4-dideoxy-1,4-imino-D-mannitol.

The N-alkylation with butanal is preferably carried out under a hydrogen atmosphere in the presence of a palladium black catalyst and ethanol solvent medium. The N-alkylation with benzyl bromide is preferably carried out together with potassium carbonate in DMF solvent medium. It will be appreciated that other N-alkyl derivatives can be made in an analogous manner by substituting other aldehydes for the butanal in the foregoing reaction.

The fluoride ion in the fluoro displacement reaction is preferably provided by tetrabutylammonium fluoride. The acid hydrolysis to remove isopropylidene protecting groups is preferably carried out with aqueous trifluoroacetic acid.

Other suitable reactants and solvents for use in the above synthesis reactions will be readily apparent to the person skilled in the art.

As used herein, compound numbers in parentheses correspond to compounds shown by chemical structure as follows:

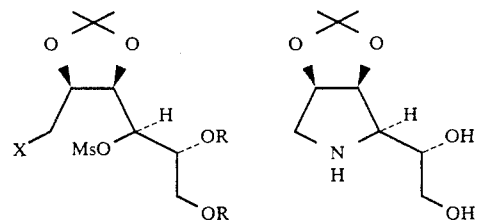

(1) X = OMs; R,R = CMe$_2$
(2) X = N$_3$; R,R = CMe$_2$
(3) X = N$_3$; R,R = H (6)

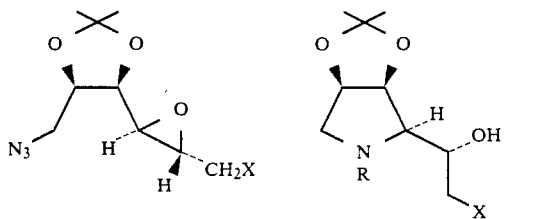

(4) X = OH
(5) X = OSO$_2$CF$_3$
(7) X = F
(10) X = Br (8) X = F; R = H
(11) X = H; R = H
(13) X = H; R = Me
(15) X = H; R = Bu
(17) X = H; R = CH$_2$Ph

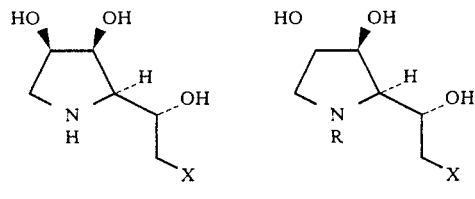

(19) X = OH
(9) X = F
(12) X = H

(14) R = Me
(16) R = n-Bu
(18) R = CH$_2$Ph

DETAILED DESCRIPTION OF THE INVENTION

The following examples will further illustrate the invention in greater detail although it will be appreciated that the invention is not limited to these specific examples. The starting dimesylate (1) was synthesized as described by Fleet et al., *Tetrahedron* 44, 2649-2655 (1988), by converting diacetone mannose into the corresponding diol, 1,2:4,5-di-O-isopropylidene-D-mannitol, and then esterifying the diol with methanesulfonyl chloride to give dimesylate (1).

Examples 1 to 3 illustrate the synthesis of the divergent intermediate, 4,5-anhydro-1-azido-1-deoxy-2,3-O-isopropylidene-D-talitol (4), from the dimesylate (1). Example 4 illustrates the synthesis of the triflate derivative (5), whereas Example 5 illustrates the synthesis of the diol, 1,4-dideoxy-1,4-imino-2,3-O-isopropylidene-D-mannitol (6), both from the divergent intermediate triflate (4). Examples 6 to 8 illustrate the synthesis of 6-fluoro-1,4-imino-1,4, 6-trideoxy-D-mannitol, whereas Examples 9 to 11 illustrate the synthesis of 1,4-imino-1,4,6-trideoxy-D-mannitol, both from the triflate derivative (5). Examples 12 to 17 illustrate the preparation of various N-alkylated derivatives of 1,4-dideoxy-1,4-imino-D-mannitol (19) from the divergent intermediate diol (6), including the novel N-butyl and N-benzyl derivatives, (16) and (18), respectively.

METHODS

Melting points were recorded on a Kofler hot block and are uncorrected. Infrared spectra were recorded on a Perkin-Elmer 297 spectrophotometer or a Perkin-Elmer 1750 FT spectrophotometer as a thin film unless otherwise stated. $^1$H NMR spectra were run at 300 MHZ on a Bruker WH 300 spectrometer (500 MHz on a Bruker AM 500 spectrometer). $^{13}$C NMR spectra were recorded on a Varian Gemini 200 (50 MHz) or a Bruker 250 (62.9 MHz) spectrometer. Multiplicities were assigned using DEPT sequence on the Gemini and by off resonance decoupling on the Bruker. Spectra were run in deuteriochloroform unless otherwise stated, using residual protonated solvent as an internal standard. $^{13}$C D$_2$O spectra use 1,4-dioxane or methanol as the internal standard. Mass spectra were recorded on VG Micromass 30F, ZAB IF or Masslab 20-250 spectrometers. Desorption chemical ionization (DCI, NH$_3$) and chemical ionization (CI, NH$_3$) techniques were used. Optical rotations were measured on a Perkin-Elmer 241 polarimeter with a path length of 1 dm. Concentrations were given in g/100 ml. Microanalyses were performed by the microanalysis service of the Dyson-Perrins laboratory, Oxford, U.K. Thin layer chromatography (t.l.c.) was carried out on aluminum sheets pre-coated with 60F$_{254}$ silica. Plates were developed using either 5% v/v concentrated sulphuric acid in methanol, 0.2% w/v cerium (IV) sulphate and 5% ammonium molybdate in 2M sulphuric acid or 0.5% ninhydrin in methanol. Flash chromatography was carried out using Merck Keiselgel 60 (0.04-0.063 mm). Solvents were dried according to the following procedures: Dichloromethane was refluxed over and distilled from calcium hydride. N,N-dimethylformamide was distilled under reduced pressure from calcium hydride. Methanol was distilled from magnesium methoxide. Pyridine was distilled from and stored over potassium hydroxide. Tetrahydrofuran was distilled from a purple solution of sodium benzophenone ketyl immediately before use. Hexane was distilled at 68° C. before use to remove involatile fractions. Hydrogenations were executed at atmospheric pressure of hydrogen gas maintained by inflated balloon.

EXAMPLE 1

1-Azido-deoxy-2,3:5,6-di-O-isopropylidene-4-O-methanesulphonyl-D-mannitol (2)

To the dimesylate (1) (13 g, 31 mmol) in dimethylformamide:water (9:1, 130 ml) was added all at once sodium azide (6 g, 93 mmol). The reaction mixture was then stirred at 90° C. for 18 hours. T.l.c. (50%, ethyl acetate/hexane) then showed starting material (R$_f$0.35) and product (R$_f$0.55). The solvent was then removed in vacuo to give a pale brown residue which was taken up in ether (150 ml) and washed with water (100 ml). The water was then back extracted with ether (50 ml). The combined ethereal extracts were then washed with brine (4×50 ml) before being dried (sodium sulphate). Removal of the solvent followed by flash chromatography (0-80%, ethyl acetate/hexane) gave 1-azido-1-deoxy-2,3:5,6-di-O-isopropylidene-4-O-methanesulphonyl-D-mannitol (2), (7g, 62%) as a colourless oil. $v_{max}$: 2104 cm$^{-1}$. $^1$H NMR ∂: 4.75 (1H, t, H-4), 4.4-4.0 (5H, m, H-2, H-3, H-5, H-6, H-6'), 3.5 (2H, m, H-1, H-1'), 3.17 (3H, s, SCH$_3$), 1.57, 1.44, 1.40, 1.36 (12H, 4s, CH$_3$). $^{13}$C NMR ∂: 110.5, 109.4 (2s, C(CH$_3$)$_2$), 78.8, 76.6, 76.2, 74.8

(4d, C-2, C-3, C-34, C-5), 67.0 (t, C-6), 50.9 (t, C-1), 39.0 (q, SCH$_3$), 27.4, 25.8, 25.5, 24.8 (4q, CH$_3$). m/z (DCI, NH$_3$): 383 (M+NH$_4^+$, 15%), 338 (M+H-N$_2^+$, 100%). Starting dimesylate was also recovered (3.8 g, 30%).

EXAMPLE 2

1-Azido-1-deoxy-2,3-O-isopropylidene-4-O-methanesulphonyl-D-mannitol (3)

To the azidomesylate (2) (10 g, 27.4 mmol) was added methanol:water (10:1, 33 ml), followed by camphorsulphonic acid (30 mg). The solution was then stirred for 2 hours at 50° C. by which time t.l.c. (50%, ethyl acetate/hexane) showed the reaction to be about 30% complete. The acid was then neutralised with 0.880 ammonia solution before the solvent was removed in vacuo. Preadsorption onto silica gel and purification by flash chromatography (30% ethyl acetate/hexane followed by neat ethyl acetate) gave starting material and product. The recovered starting material was then twice recycled by the same procedure to give 1-azido-1-deoxy-2,3-O-isopropylidene-4-O-methanesulphonyl-D-mannitol (3), (5 g, 56%) m.p. 82°–84° C. (ethyl acetate/hexane). [α]$_D^{20}$+90.8° (c, 0.51 in CHCl$_3$). ν$_{max}$: 3400, 2104 cm$^{-1}$. $^1$H NMR ∂: 4.80 (1H, t, H-4), 4.43 (2H, m, H-2, H-3), 3.90–3.72 (3H, m, H-5, H-6, H-6'), 3.54 (2H, d, H-1, H-1'), 3.18 (3H, SCH$_3$), 2.90 (1H, d, OH), 2.30 (1H, t, OH), 1.55, 1.41 (6H, 2s, CH$_3$). $^{13}$C NMR ∂: 109.0 (s, C(CH$_3$)$_2$), 78.7, 76.5, 71.9 (3d, C-2, C-3, C-4, C-5), 62.1 (t, C-6), 51.1 (t, C-1), 38.9 (q, SCH$_3$), 27.4, 25.4 (2q, CH$_3$). m/z (DCI, NH$_3$): 343 (M+NH$_4^+$, 50%), 298 (M+H-N$_2^+$, 100%), 202 (M+H-N$_2$-HOSO$_2$Me$^+$, 40%), 142 ((202-HOCH$_2$CHOH)$^+$, 40%). (Found C, 36.66; H, 5.83; N, 12.63%. C$_{10}$H$_{19}$N$_3$O$_7$S requires C, 36.92; H, 5.85; N, 12.92%) and starting material (3.1 g, 31%).

EXAMPLE 3

4,5-Anhydro-1-azido-1-deoxy-2,3-O-isopropylidene-D-talitol (4)

To the diol (3) (2.88 g, 8.86 mmol) in freshly distilled, dry methanol (20 ml) was added a saturated barium methoxide solution (4 ml). The reaction was then stirred for 30 minutes at room temperature by which time no starting material (R$_f$ 0.2) remained and only one product (R$_f$ 0.25) was visible by t.l.c. (50%, ethyl acetate/hexane). Carbon dioxide (solid) was then added followed by silica gel. Removal of the solvent in vacuo and flash chromatography (0–70%, ethyl acetate/hexane) then gave 4,5-anhydro-1-azido-1-deoxy-2,3-O-isopropylidene-D-talitol (4), as a colourless oil (1.9 g, 95%). [α]$_D^{20}$+77.3° (c, 0.51 in CHCl$_3$). ν$_{max}$: 3500, 2104 cm$^{-1}$. $^1$H NMR ∂: 4.38 (1H, m, H-2), 4.08–3.62 (3H, m, H-3, H-6, H-6'), 3.54 (2H, m, H-1, H-1'), 3.09 (2H, m, H-4, H-5), 2.30 (1H, s, OH), 1.50, 1.35 (6H, 2s, CH$_3$). $^{13}$C NMR ∂: 110.0 (s, C(CH$_3$)$_2$), 76.5, 76.4, (2d, C-2, C-3), 60.8 (t, C-6), 57.6 (d, C-5), 52.3 (2d, C-4, C-5), 50.3 (t, C-1), 27.2, 24.7 (2q, CH$_3$). m/z (DCI, NH$_3$): 247 (M+NH$_4^+$, 5%), 230 (M+H$^+$, 4%), 202 (M+H-N$_2^+$, 70%), 184 (M+H-N$_2$-H$_2$O$^+$, 50%), 142 (100%).

EXAMPLE 4

4,5-Anhydro-1-azido-1-deoxy-2,3-O-isopropylidene-6-O-trifluoromethanesulphonyl-D-talitol (5)

To a solution of the epoxy alcohol (4) (1.9 g, 8.6 mmol) in freshly distilled, dry dichloromethane (40 ml) at −30° C. was added dry pyridine (1.4 ml, 17.2 mmol) followed by trifluoromethanesulphonic anhydride (2.2 ml, 13 mmol). The reaction mixture was then stirred for 15 minutes at this temperature by which time t.l.c. showed no starting material (R$_f$ 0.25) and one product (R$_f$ 0.85). The solution was then washed with dilute aqueous hydrochloric acid (10 ml), saturated copper (II) sulphate solution (10 ml) and brine (20 ml) before being dried (sodium sulphate). Removal of the solvent in vacuo then gave 4,5-anhydro-1-azido-1-deoxy-2,3-O-isopropylidene-6-O-trifluoromethanesulphonyl-D-talitol (5), as a yellow oil which was used immediately without further purification. $^1$H NMR ∂: 4.82 (1H, dd, H-6), 4.40 (2H, m, H-2, H-6'), 3.88 (1H, t, H-3), 3.55 (2H, dd, H-1, H-1'), 3.31 (1H, dt, H-5), 3.1 (1H, dd, H-4), 1.52, 1.38 (6H, 2s, CH$_3$). $^{13}$C NMR ∂: 110.0 (s, C(CH$_3$)$_2$), 76.2 (d, C-2), 75.9 (d, C-3), 75.2 (t, C-6), 53.1 (2d, C-4, C-5), 49.9 (t, C-1), 27.0, 24.5 (2q, CH$_3$).

EXAMPLE 5

1,4-dideoxy-1,4-imino-2,3-O-isopropylidene-D-mannitol (6)

The epoxide (4) (1.8 g, 8.4 mmol) was stirred in 1,4-dioxane:water (1:1, 20 ml) under hydrogen in the presence of 10% palladium on carbon (100 mg) for 18 hours by which time no starting material (R$_f$ 0.25) remained by t.l.c. (50%, ethyl acetate/hexane). Filtration and evaporation then gave the crude aminodiol which was purified by ion exchange chromatography to give 1,4-dideoxy-1,4-imino-2,3-O-isopropylidene-D-mannitol (6), as an oil which crystallised on standing (1.55 g, 90%). This was shown to be identical to authentic material. m.p. 86°–88° C. (lit. 86°–88° C.)

EXAMPLE 6

4,5-Anhydro-1-azido-1,6-dideoxy-6-fluoro-2,3-O-isopropylidene-D-talitol (7)

To the triflate (5) prepared from the diol (4) (1 g 3.0 mmol) in dry, freshly distilled, tetrahydrofuran (20 ml) was added tetrabutylammonium fluoride (1.5 g 4.5 mmol). The reaction was then stirred for 2 hours at room temperature after which time t.l.c. (25%, ethyl acetate/hexane) showed no change. Silica gel was then added and the solvent removed in vacuo. Purification by flash chromatography (0–30%, ethyl acetate/hexane) then gave 4,5-anhydro-1-azido-1,6-dideoxy-6-fluoro-2,3-O-isopropylidene-D-talitol (7), as a colourless oil (547 mg, 77%). [α]$_D^{20}$+67.6° (c, 0.74 in CHCl$_3$). ν$_{max}$: 2109 cm$^{-1}$. $^1$H NMR ∂: 4.71 (1H, dd, H-6, J$_{5,6}$ 2.3 Hz, J$_{6,6'}$ 10.9 Hz, J$_{H,F}$ 47.6 Hz), 4.41 (1H, ddd, H-2, J$_{1,2}$ 4.1 Hz, J$_{1',2}$ 6.7 Hz, J$_{2,3}$ 7.0 Hz), 4.39 (1H, dd, H-6', J$_{5,6'}$ 5.4 Hz, J$_{H,F}$ 46.8 Hz), 3.85 (1H, dd, H-3, J$_{3,4}$ 7.0 Hz), 3.57 (2H, ABX, H-1, H-1', J$_{1,1'}$ 13.1 Hz), 3.24 (1H, m, H-5, J$_{H,F}$ 13.7 Hz), 3.05 (1H, dd, H-4, J$_{4,5}$ 3.0 Hz, J$_{H,F}$ 1.3 Hz), 1.53, 1.38 (6H, 2s, CH$_3$). $^{13}$C NMR ∂: 109.9 (s, CMe$_2$), 81.8 (t, C-6, J$_{C,F}$ 171 Hz), 76.4, 76.3 (2d, C-2, C-3), 55.0 (d, C-5, J$_{C,F}$ 23 Hz), 52.1 (d, C-4, J$_{C,F}$ 8 Hz), 50.2 (t, C-1), 27.2, 24.8 (2q, CH$_3$). m/z (DCI, NH$_3$): 249 (M+NH$_4^+$, 5%), 216 (M+NH$_4$-CH$_2$F$^+$, 35%), 204 (M+H-N$_2^+$, 100%). (Found C, 46.75; H, 6.33; N, 17.60%. C$_9$H$_{14}$N$_3$O$_3$F requires C, 46.75; H, 6.06; N, 18.18%).

EXAMPLE 7

6-Fluoro-1,4-imino-2,3-O-isopropylidene-1,4,6-trideoxy-D-mannitol (8)

The epoxide (7) (490 mg, 2.1 mmol) was stirred in ethanol (20 ml) under hydrogen in the presence of 10% palladium on carbon (50 mg) for 18 hours by which time no starting material ($R_f$ 0.3) remained by t.l.c. (50%, ethyl acetate/hexane). Filtration and evaporation then gave the crude aminoalcohol as a white solid which was purified by recrystallisation to give 6-fluoro-1,4-imino-2,3-O-isopropylidene-1,4,6-trideoxy-D-mannitol (8), as a white solid (380 mg, 87%). m.p. >210° C. $[\alpha]_D^{20}$ −40.0° (c, 0.41 in MeOH). $\nu_{max}$ (KBr): 3285 cm$^{-1}$. $^1$H NMR (D$_2$O) ∂: 4.94 (2H, m, H-2, H-3), 4.60 (1H, m, H-6), 4.42 (1H, m, H-5), 4.22 (1H, m, H-6'), 3.46 (2H, m, H-1, H-4), 3.24 (1H, m, H-1'), 1.39, 1.24 (6H, 2s, CH$_3$). $^{13}$C NMR ∂: 111.8 (s, CMe$_2$), 86.5 (t, C-6, $J_{C,F}$ 166 Hz), 81.4, 81.1 (2d, C-2, C-3), 68.9 (d, C-5, $J_{CF}$ 18 Hz), 62.9 (d, C-4, $J_{C,F}$ 6 Hz), 52.0 (t, C-1), 25.2, 23.6 (2q, CH$_3$). m/z (DCI, NH$_3$): 206 (M+H$^+$, 100%), 142 (M+H-FH$_2$CCH$_2$OH$^+$, 35%). (N.B:-Proton under HOD suppression)

EXAMPLE 8

6-Fluoro-1,4-imino-1,4,6-trideoxy-D-mannitol (9)

The fluoride (8) (180 mg, 0.87 mmol) was dissolved in trifluoroacetic acid:water (9:1, 4 ml) and stirred for 48 hours at room temperature. Removal of the solvent in vacuo and purification by ion exchange chromatography with Dowex 50(H) followed by Amberlite CG-400(Cl) to gave 6-fluoro-1,4-imino-1,4,6-trideoxy-D-mannitol (9), as a gum which was recrystallised (85 mg, 70%). m.p. 99°-100° C. (methanol/diethyl ether). $[\alpha]_D^{20}$−17.5° (c, 0.23 in MeOH). $\nu_{max}$: 3270 cm$^{-1}$. $^1$H NMR ∂: 4.45 (1H, dd, H-6, $J_{H,F}$47.2 Hz, $J_{6,5}$2.3 Hz, $J_{6,6'}$10.4 Hz), 4.36 (1H, dd, H-6', $J_{H,F}$47.2 Hz, $J_{5,6'}$4.5 Hz), 4.17 (1H, ddd, H-2, $J_{2,3}$3.8 Hz, $J_{1,2}$8.2 Hz, $J_{1',2}$8.2 Hz), 4.04 (1H, t, H-3, $J_{3,4}$3.8 Hz), 3.84 (1H, ddd, H-5, $J_{H,F}$26.4 Hz, $J_{4,5}$9.7 Hz), 3.04 (1H, dd, H-4), 3.00 (1H, dd, H-1, $J_{1,1'}$11.2 Hz), 2.60 (1H, dd, H-1'). $^{13}$C NMR ∂: 86.3 (t, C-6, $J_{C,F}$165.6 Hz), 72.9 (2d, C-2, C-3), 69.7 (d, C-5, $J_{C,F}$18.2 Hz), 60.2 (d, C-4, $J_{C,F}$6.9 Hz), 49.1 (t, C-1). m/z (DCI, NH$_3$): 166 (M+H$^+$, 100%), 146 (M+H-HF$^+$, 35%), 102 (M+H-FH$_2$CCH$_2$OH$^+$, 20%). (Found C, 43.53; H, 7.55; N, 8.22%. C$_6$H$_{12}$NO$_3$F requires C, 43.64; H, 7.27; N, 8.48%).

EXAMPLE 9

4,5-Anhydro-1-azido-6-bromo-1,6-dideoxy-2,3-O-isopropylidene-D-talitol (10)

To the triflate(5) prepared from the diol (4) (0.68 g 2.0 mmol) in dry, freshly distilled, tetrahydrofuran (10 ml) cooled to −10° C. was added lithium bromide (200 mg, 2.4 mmol). The reaction was then allowed to rise to room temperature over 2 hours after which time t.l.c. (25%, ethyl acetate/hexane) showed no starting material ($R_f$0.4) and one product ($R_f$0.45). Silica gel was then added and the solvent removed in vacuo. Purification by flash chromatography (0–30%, ethyl acetate/hexane) then gave 4,5'-anhydro-1-azido-6-bromo-1,6-dideoxy-2,3-O-isopropylidene-D-talitol (10), as a white solid (449 mg, 74%). m.p. 60°-61° C. $[\alpha]_D^{20}$+63.5° (c, 0.7 in CHCl$_3$). $\nu_{max}$(KBr): 2103 cm$^{-1}$. $^1$H NMR ∂: 4.40 (1H, m, H-2), 3.84 (1H, dd, H-3), 3.64-3.36 (4H, m, H-1, H-1', H-4, H-5), 3.27 (1H, m, H-6), 3.03 (1H, dd, H-6'). $^{13}$C NMR ∂: 110.2 (s, CMe$_2$), 76.4 (d, C-2, C-3), 57.0 (d, C-5), 56.3 (d, C-4), 50.2 (t, C-1), 31.0 (t, C-6), 27.3. 24.8 (2q, CH$_3$). m/z (DCI, NH$_3$): 2.78, 276 (M+H-O$^+$, 40%), 266, 264 (M+H-N$_2^+$, 100%), 237, 235 (M+NH$_4$-H$_2$O-CH$_2$N$_3^+$, 35%), 142 (237-CH$_2$Br, 75%), 84 (142CH$_3$COCH$_3$, 100%). (Found C, 37.15; H, 4.89; H, 14.18; N, 14.18%. C$_9$H$_{14}$N$_3$O$_3$Br requires C, 36.99; H, 4.79; N, 14.38%).

EXAMPLE 10

1,4-Imino-2,3-O-isopropylidene-1,4,6-trideoxy-D-mannitol (11)

The bromoepoxide (10) (280 mg, 0.95 mmol) was stirred under an atmosphere of hydrogen in dioxan:water (2:1, 10 ml) with poly-4-vinylpyridine (280 mg) and 10% palladium on carbon (70 mg) for 12 hours. T.l.c. (50%, ethyl acetate/hexane) then showed no starting material ($R_f$0.95). Filtration followed by removal of the solvent in vacuo and purification by flash chromatography (0–25%, methanol/ethyl acetate) then gave 1,4-imino-2,3-O-isopropylidene-1,4,6-trideoxy-D-mannitol (11). (120 mg, 68%) as a white solid which was recrystallised. m.p. >200° C. (methanol/diethyl ether). $[\alpha]_D^{20}$+8.6 (c, 0.15 in MeOH). $\nu_{max}$ (KBr): 3480, 3413 cm$^{-1}$. $^1$H NMR ∂: 4.90 (2H, m, H-2, H-3), 4.06 (1H, dq, H-5), 3.39 (1H, d, H-1), 3.19 (2H, m, H-1', H-4), 1.38, 1.23 (6H, 2s, C(CH$_3$)$_2$), 1.21 (3H, d, CH$_3$). $^{13}$C NMR ∂: 112.4 (s, CMe$_2$), 80.9, 80.5 (2d, C-2, C-3), 68.9, 65.7 (2d, C-4, C-5), 51.8 (t, C-1), 25.4, 23.7 (2q, C(CH$_3$)$_2$).

EXAMPLE 11

1,4-Imino-1,4,6-trideoxy-D-mannitol (12)

The amine (11) (45 mg, 0.24 mmol) was stirred in trifluoroacetic acid:water (1:1, 2 ml) for 24 hours. The solvent was then removed in vacuo and the resultant solid purified by ion exchange chromatography with Dowex 50(H) followed by Amberlite CG-400(Cl) to give 1,4-imino-1,4,6-trideoxy-D-mannitol (12). which was acidified with dilute aqueous hydrochloric acid and recrystallised (32 mg, 90%). m.p. 182°-184° C. (ethanol/diethyl ether) (lit.[20,21] 184°-185° C.). $[\alpha]_D^{20}$−25.6° (c, 0.19 in MeOH (lit. −21.5°). $\nu_{max}$ (KBr): 3413, 1227, 1131 cm$^{-1}$. $^1$H NMR ∂: 4.35 (1H, ddd, H-2, $J_{2,3}$ 3.5 Hz, $J_{1,2}$ 8.5 Hz, $J_{1',2}$ 8.5 Hz), 4.24 (1H, t, H-3, $J_{3,4}$3.5 Hz), 4.05 (1H, dq, H-5), 3.45 (1H, dd, H-1, $J_{1,1'}$ 12.0 Hz), 3.28 (1H, dd, H-4, $J_{4,5}$ 8.5 Hz), 3.03 (1H, dd, H-1'), 1.17 (3H, d, CH$_3$, $J_{5,6}$ 6.4 Hz). $^{13}$C NMR (D$_2$O) ∂: 70.7, 70.2 (2d, C-2, C-3), 66.5, 63.5 (2d, C-4, C-5), 47.5 (t, C-1), 19.9 (q, C-6).

EXAMPLE 12

1,4-Dideoxy-1,4-imino-2,3-O-isopropylidene-N-methyl-D-mannitol (13)

To the diol(6) (100 mg, 0.5 mmol) in methanol (5 ml) under an atmosphere of hydrogen with palladium black (50 mg) was added formaldehyde solution (37–40%, 40 µl, 0.75 mmol). The reaction was then stirred for 12 hours by which time t.l.c. (20%, methanol/chloroform) showed some starting material ($R_f$0.4) and product ($R_f$0.55). Filtration followed by removal of the solvent in vacuo then gave an oil which was purified by flash chromatography (0–10%, methanol/chloroform) to give 1,4-dideoxy-1,4-imino-2,3-O-isopropylidene-N-methyl-D-mannitol (13), (30 mg) and starting material. $[\alpha]_D^{20}$−65.1° (c 0.37 in CHCl$_3$). $^1$H NMR ∂: 4.74 (1H, m, H-3), 4.61 (1H, m, H-2), 4.00 (1H, m, H-5), 3.83 (2H, m, H-4, H-6), 3.25 (1H, d, H-6'), 2.34 (3H, s, CH$_3$), 2.15 (1H, dd, H-1), 1.94 (1H, dd, H-1'), 1.54, 1.30 (6H, 2s, C(CH$_3$)$_2$). $^{13}$C NMR ∂: 111.2 (s, CMe$_2$), 81.4, 77.7 (2d, C-2, C-3), 69.9, 69.4 (2d, C-4, C-5), 65.3 (t, C-6), 61.5 (t, C-1), 39.4 (q, NCH$_3$), 25.8, 24.0 (2q, C(CH$_3$)$_2$). m/z (CI, NH$_3$): 218 (M+H$^+$, 100%), 156 (M-HOCH$_2$CH$_2$OH$^+$, 50%).

EXAMPLE 13

1,4-Dideoxy-1,4-imino-N-methyl-D-mannitol (14)

The methylated compound (13) (30 mg, 0.14 mmol) was stirred in trifluoroacetic acid:water (1:1, 0.5 ml) for 48 hours. Removal of the solvent in vacuo and purification by ion exchange chromatography then gave the free base as a gum. Addition of dilute aqueous hydrochloric acid then gave the hydrochloride salt of 1,4-Dideoxy-1,4-imino-N-methyl-D-mannitol (14), which was recrystallised. (15 mg, 50%). m.p. 154°–156° C. (methanol/diethyl ether). $^1$H NMR ∂: 4.35 (2H, m, H-2, H-3), 4.00 (1H, q, H-5), 3.63 (2H, m, H-4, H-6), 3.40 (2H, m, H-1, H-6'), 3.30 (1H, dd, H-1), 2.77 (3H, s, NCH$_3$). $^{13}$C NMR ∂: 71.8, 70.5 (2d, C-2, C-3), 69.5, 68.0 (2d, C-4, C-5), 63.5 (t, C-6), 59.3 (t, C-1), 40.8 (q, NCH$_3$). m/z (DCI, NH$_3$): 178 (M+H$^+$, 100%), 116 (M-HOCH$_2$CH$_2$OH$^+$, 50%). (Found C, 39.53; H, 7.77: N, 6.49% C$_7$H$_{16}$NO$_4$Cl required C, 39.34: 7.49; N, 6.56%).

EXAMPLE 14

N-Butyl-1,4-dideoxy-1,4-imino-2,3-O-isopropylidene-D-mannitol (15)

To the diol (6) (100 mg, 0.5 mmol) in ethanol (5 ml) under an atmosphere of hydrogen with pallidium black (100 mg) was added butanal (1 ml, 16.9 mmol). The reaction was then stirred for 24 hours by which time t.l.c. (20%, methanol/chloroform) showed some starting material (R$_f$0.4) and product (R$_f$0.85). Filtration followed by removal of the solvent in vacuo then gave an oil which was purified by flash chromatography (0–10%, methanol-chloroform) to give N-Butyl-1,4-dideoxy-1,4-imino-2,3-O-isopropylidene-D-mannitol (15), (30 mg) and starting material. $\nu_{max}$(CHCl$_3$): 3500 cm$^{-1}$. $^1$H NMR ∂: 4.73 (1H, m, H-3), 4.63 (1H, m, H-2), 4.05 (1H, m, H-5), 3.8 (2H, m, H-4, H-6), 3.5 (1H, d, OH), 3.30 (1H, d, H-6'), 2.90 (1H, m, H-1), 2.1 (3H, m, H-1', NCH$_2$), 1.6–1.25 (4H, m, CH$_2$CH$_2$)1.49, 1.30 (6H, 2s, C(CH$_3$)$_2$), 0.92 (3H, t, CH$_3$). C NMR ∂: 111.4 (s, CMe$_2$), 81.2, 77.6 (2d, C-2, C-3), 69.6 (d, C-5), 67.9 (d, C-4), 65.3 (t, C-1), 52.1 (t, NCH$_2$), 29.5 (t, CH$_2$), 25.8, 24.4 (2q, C(CH$_3$)$_2$), 20.3 (t, CH$_2$), 13.8 (q, CH$_3$).

EXAMPLE 15

N-Butyl-1,4-dideoxy-1,4-imino-D-mannitol (16)

The butyl compound (15) (30 mg, 0.14 mmol) was stirred in trifluoroacetic acid:water (1:1, 0.5 ml) for 48 hours. Removal of the solvent in vacuo and purification by ion exchange chromatography then gave the free base as a colourless gum (17 mg, 67%). $\nu_{max}$(KBr): 3400 cm$^{-1}$. $^1$ HMR ∂: 4.12 (2H, m, H-2, H-3), 3.80 (1H, m, H-5), 3.58 (2H, m, H-6, H-6'), 2.83 (1H, m, H-4), 2.72 (2H, m, H-1, H-1'), 2.56 (1H, m, NCH), 2.29 (1H, m, NCH), 1.31 (2H, m, CH$_2$), 1.13 (2H, m, CH$_2$), 0.75 (3H, t, CH$_3$).

EXAMPLE 16

1,4-dideoxy-1,4-imino-2,3-O-isopropylidene-N-benzyl-D-mannitol (17)

To the amine diol (6) (100 mg, 0.5 mmol) in freshly distilled, dry dimethylformamide (5 ml) was added potassium carbonate (200 mg, 1.5 mmol) and benzyl bromide (64 µl, 0.55 mmol). The reaction mixture was then stirred for 2 hours at room temperature by which time t.l.c. (20%, methanol/chloroform) showed no starting material (R$_f$0.4) and one product (R$_f$0.85). The solvent was then removed in vacuo and the product preadsorbed onto silica gel. Purification by flash chromatography (0–5%, methanol/chloroform) then gave 1,4-dideoxy-1,4-imino-2,3-O-isopropylidene-N-benzyl-D-mannitol (17), as a colourless oil (100 mg, 70%). $[\alpha]_D^{20}$ −72.1° (c 0.58 in CHCl$_3$). $\nu_{max}$: 3400, 755 cm$^{-1}$. $^1$H NMR ∂: 7.3 (5H, m, ArH), 4.75 (1H, m, H-2), 4.55 (1H, t, H-3), 4.2 (2H, m, H-5, H-6), 3.85 (2H, m, H-4, H-6'), 3.65 (1H, m, OH), 3.02 (3H, m, H-1, h-1', OH), 2.30 (1H, t, PhCH), 2.10 (1H, dd, PhCH), 1.55, 1.32 (6H, 2s, CH$_3$). $^{13}$C NMR ∂: 138 (s, Ar), 128.9, 127.1 (3d, Ar), 111.4 (s, CMe$_2$), 81.2, 77.6 (2d, C-2, C-3), 69.9 (d, C-5), 66.9 (d, C-4), 65.2 (t, C-6), 58.3 (t, C-1), 56.1 (t, PhCH$_2$), 25.9, 24.5 (2q, CH$_3$). m/z (CI, NH$_3$): 294 (M+H$^+$, 100%), 232 (M-HOCH$_2$CH$_2$OH$^+$, 30%). (Found C, 65.57; H, 8.21; N, 5.18% C$_{16}$H$_{23}$NO$_4$ required C, 65.57; H, 7.82; N, 4.78%).

EXAMPLE 17

N-Benzyl-1,4-dideoxy-1,4-imino-D-mannitol (18).

The diol (17) (70 mg, 0.24 mmol) was stirred in triflouroacetic acid:water (1:1, 2 ml) for 48 hours at room temperature. The solvent was then removed in vacuo and the resultant gum purified by ion exchange chromatography to give, after freeze drying N-Benzyl-1,4-dideoxy-1,4-imino-D-mannitol (18), as a colourless gum. $[\alpha]_D^{20}$ −42.8° (c 0.14 in MeOH). $\nu_{max}$: 3895, 750 cm$^{-1}$. $^1$H NMR ∂: 7.2 (5H, m, ArH), 4.18 (1H, t, H-3, J$_{1,2}$ 5.1 Hz), 3.99 (1H, m, H-2), 3.77 (2H, m, H-5, H-6), 3.62 (2H, m, H-4, H-6'), 3.43 (1H, d, H-1), 2.86 (1H, t, H-1'), 2.67 (2H, m, PhCH$_2$). $^{13}$C NMR ∂: 137 (s, Ar), 130.8, 129.5, 128.7 (3d, Ar), 73.2, 71.6, 70.4 (3d, C-2, C-3, C-5), 66.5 (d, C-4), 64.1 (t, C-6), 60.0 (t, C-1), 56.1 (t, PhCH$_2$). (Found C, 61.61; H, 7.23; N, 5.23% C$_{13}$H$_{19}$NO$_4$ required C, 61.66; H, 7.51; N, 5.53%).

EXAMPLE 18

Glycosidase Inhibition Tests

The novel derivatives of 1,4-dideoxy-1,4-imino-D-mannitol described herein were tested as inhibitors of human liver glycosidases and the effects compared with those of known inhibitors, e.g. swainsonine and the underivatized 1,4-dideoxy-1,4-imino-D-mannitol by conventional enzyme assay methods described by Daher et al., Biochem. J. 258, 613 (1989). The results are set forth in Table 1 below in which it can be seen that although the N-methyl derivative is less effective than the underivatized material, the 6-fluoro derivative unexpectedly has substantially greater potency.

TABLE 1

| | SWAINSONINE ANALOGUES-DIM SERIES | | | |
|---|---|---|---|---|
| Compound | Lysosomal | Neutral | Golgi | Other enzymes |
| Swainsonine | 100% k$_i$ 70 nM | 89% (93G) | 98% | α-Gal 56% β-Gal 58% α-Fuc 61% |
| DIM | 59% k$_i$ 1.3 × 10$^{-5}$ | 96% | 84% | Nil |

TABLE 1-continued

| SWAINSONINE ANALOGUES-DIM SERIES | | | | |
|---|---|---|---|---|
| Compound | Lysosomal | Neutral | Golgi | Other enzymes |
| N-methyl-DIM | 26% | 54% | 42% | Nil |
| N-butyl-DIM | 5% | 14% | 61% | $\beta$-Gluc 20% $\alpha$-Fuc 10% |
| N-benzyl-DIM | 34% | 44% | 72% | $\beta$-Gluc 70% |
| 6-Fluoro-DIM | 98% $I_{50}$ 1.1 $\mu$M | 91% | 89% | $\beta$-Gluc 22% $\beta$-Gal 78% $\alpha$-Ara 65% $\beta$-Xyl 26% |

DIM = 1,4-Dideoxy-1,4-imino-D-mannitol

Various other examples will be apparent to the person skilled in the art after reading the present disclosure without departing from the spirit and scope of the invention. It is intended that all such other examples be included within the scope of the appended claims.

What is claimed is:

1. N-butyl-1,4-dideoxy-1,4-imino-D-mannitol.
2. N-Benzyl-1,4-dideoxy-1,4-imino-D-mannitol.
3. A method for the synthesis of the N-butyl or N-benzyl derivative of 1,4-dideoxy-1,4-imino-D-mannitol comprising:
    (a) catalytically hydrogenating 4,5-anhydro-1-azido-1-deoxy-2,3-O-isopropylidene-D-talitol to give a corresponding diol,
    (b) chemically alkylating the diol with butanal to form a protected N-butyl derivative or with benzyl bromide to form a protected N-benzyl derivative, and
    (c) removing the isopropylidene protecting group by acid hydrolysis to give, respectively, the N-butyl or N-benzyl derivative of 1,4-dideoxy-1,4-imino-D-mannitol.
4. A method for the synthesis of the N-butyl or N-benzyl derivative of 1,4-dideoxy-1,4-imino-D-mannitol comprising:
    (a) displacing the primary mesylate of the dimesylate, 1,4-bis(O-methanesulfonyl)-2,3:5,6-di-O-isopropylidene-D-mannitol, by reacting said dimesylate with sodium azide to give an azidomesylate,
    (b) partially hydrolyzing the azidomesylate with camphorsulfonic acid to remove the isopropylidene protecting group at C-5 and C-6 to give a corresponding diol,
    (c) oxidizing the diol to give 4,5-anhydro-1-azido-1-deoxy-2,3-O-isopropylidene-D-talitol,
    (d) catalytically hydrogenating the 4,5-anhydro-1-azido-1-deoxy-2,3-O-isopropylidene-D-talitol to give a corresponding diol,
    (e) chemically alkylating the diol with butanal to form a protected N-butyl derivative or with benzyl bromide to form a protected N-benzyl derivative, and
    (f) removing the isopropylidene protecting group by acid hydrolysis to give, respectively, the N-butyl or N-benzyl derivative of 1,4-dideoxy-1,4-imino-D-mannitol.

* * * * *

UNITED STATES PATENT AND TRADEMARK OFFICE
CERTIFICATE OF CORRECTION

PATENT NO.   :   5,041,555
DATED        :   AUGUST 20, 1991
INVENTOR(S) :   GEORGE W. J. FLEET et al

It is certified that error appears in the above-identified patent and that said Letters Patent is hereby corrected as shown below:

```
At col. 3, line 25, "(13) X = H" should read
                  --(13) X = OH--.

At col. 3, line 26, "(15) X = H" should read
                  --(15) X = OH"--.

At col. 3, line 27, "(17) X = H" should read
                  --(17) X = OH--.
```

Signed and Sealed this

Eighth Day of April, 1997

Attest:

BRUCE LEHMAN

*Attesting Officer*    Commissioner of Patents and Trademarks